United States Patent
Iida et al.

[11] Patent Number: 5,773,596
[45] Date of Patent: Jun. 30, 1998

[54] PREPARATION OF GANGLIOSIDE HAVING CERAMIDE MOIETY LABELED WITH FLUORESCENCE

[75] Inventors: Takao Iida; Yutaka Ohira, both of Tsukuba, Japan

[73] Assignee: Daikin Industries, Ltd., Osaka, Japan

[21] Appl. No.: 737,828
[22] PCT Filed: May 18, 1995
[86] PCT No.: PCT/JP95/00951
§ 371 Date: Nov. 20, 1996
§ 102(e) Date: Nov. 20, 1996
[87] PCT Pub. No.: WO95/32211
PCT Pub. Date: Nov. 30, 1995

[30] Foreign Application Priority Data

May 20, 1994 [JP] Japan ................................. 6-106970

[51] Int. Cl.[6] .................................................. C07H 15/00
[52] U.S. Cl. ....................... 536/18.6; 536/17.2; 536/17.9; 536/18.5; 536/124
[58] Field of Search ................................. 536/17.2, 17.9, 536/124, 18.5, 18.6

[56] References Cited

PUBLICATIONS

Spiegel, Biochemistry, vol. 24, pp. 5947–5952 (1985).
Hakomori, J. Biol. Chem., vol. 265, pp. 18713–18716 (Nov. 1990).
Brewer et al. Biochemistry, vol. 31, pp. 1816–1820 (1992).
Song et al. Biochemistry, vol. 28, pp. 4194–4200 (1989).
Kozteb et al. Biologicheskie Membrany, vol. 6, No. 1, pp. 34–41 (1989) No Translation Provided.

*Primary Examiner*—Kathleen K. Fonda
*Attorney, Agent, or Firm*—Birch, Stewart, Kolasch & Birch, LLP

[57] ABSTRACT

A ganglioside derivative in which a ceramide moiety is labeled with a fluorescent dye represented by the formula (I):

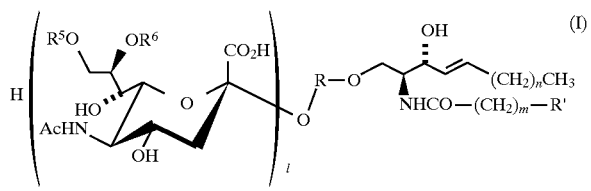

wherein —O—R—O— is a saccharide chain constituting the ganglioside, R' is an ether, sulfide, amide, urethane, thiourea or amino group having a fluorescent dye, one of $R^5$ or $R^6$ is a single bond and the other is a hydrogen atom, l is an integer of 1 to 8, m is an integer of at least 2, and n is an integer of 0 to 12. This ganglioside derivative has recognition characteristics of the saccharide chain portion and the labeling property of the fluorescent dye introduced in the ceramide moiety, and is useful as an agent for monitoring the dynamic behavior of the receptor for glycolipids, a diagnostic agent for bacteria or viruses, and the like.

3 Claims, No Drawings

PREPARATION OF GANGLIOSIDE HAVING CERAMIDE MOIETY LABELED WITH FLUORESCENCE

This is the U.S. national stage entry under 35 U.S.C. 371 of PCT/JP95/00951, filed May 18, 1995.

FIELD OF THE INVENTION

The present invention relates to a ganglioside having a fluorescently labeled ceramide moiety, intermediates for the synthesis thereof, and a process for the preparation thereof.

PRIOR ART

Glycolipids in mammalian cells belong to the group of sphingoglycolipids comprising a lipid portion called as a ceramide which consists of a sphingosine as a long chain aminoalcohol and a long chain fatty acid bonded to the sphingosine through an amide linkage, various oligosaccharide chains and a sialic acid. In particular, ganglioside is the collective name for sphingoglycolipids having a sialic acid group.

In general, most of the above ganglioside molecules are localized in the cell surfaces of animals, and the recent studies have revealed that their sialic saccharide chains are oriented outside the cells and that they play important roles in fundamental life phenomena such as discrimination in cells, reception of or response to information in cells, functions as receptors for hormones, viruses, bacteria, cell toxins, etc., intercellular distinction, proliferation and metastasis of cells, malignant alteration, immunity, and the like.

The gangliosides attract attentions as the molecules which exhibit a wide variety of physiological activities which relate to the information transfer, proliferation and metastasis of the cells.

A derivative of the ganglioside into which a fluorescent dye is introduced while maintaining its inherent physiological activities will provide a novel method for the study of cells, if such a derivative can be synthesized, since the ganglioside receptor can be identified and its behavior can be monitored visually.

A ganglioside into which fluorescein is introduced has been prepared based on the above idea. However, it has not achieved satisfactory results.

A method for detecting a bond between a ganglioside and bacteria or viruses using the ganglioside labeled with a radioisotope has been developed. However, a new method alternative to this method has been sought since this method has various problems in handling, and labeling with a fluorescence is thought to be effective.

A ganglioside labeled with a fluorescent dye will be useful as a detection and diagnostic agent for the above pathogens.

SUMMARY OF THE INVENTION

The first object of the present invention is to provide a ganglioside derivative into which a labeling dye has been introduced without deterioration of the physiological activities of the ganglioside.

The second object of the present invention is to provide an intermediate for the synthesis of such a ganglioside derivative.

The third object of the present invention is to provide processes for the preparation of such ganglioside derivative and the intermediate for the same.

According to the first aspect of the present invention, a ganglioside derivative labeled with a fluorescent dye is provided, represented by the formula (I):

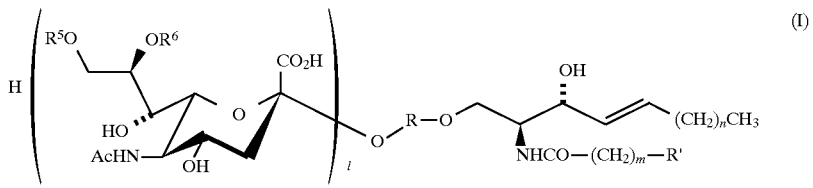

wherein —O—R—O— is a saccharide chain constituting the ganglioside, R' is an ether, sulfide, amide, urethane, thiourea or amino group having a fluorescent dye, one of $R^5$ or $R^6$ is a single bond and the other is a hydrogen atom, I is an integer of 1 to 8, m is an integer of at least 2, and n is an integer of 0 to 12.

According to the second aspect of the present invention, a ganglioside derivative labeled with a fluorescent dye is provided, represented by the formula (II):

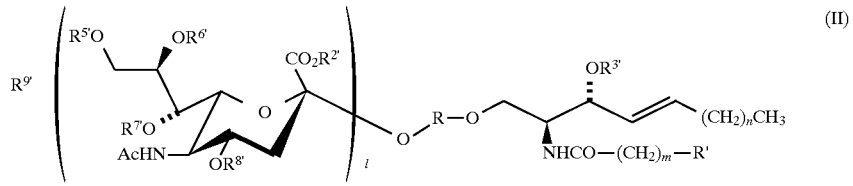

wherein $R^{2'}$ is a protecting group for a carboxylic acid, $R^{3'}$, $R^{7'}$, $R^{8'}$ and $R^{9'}$ are protecting groups for hydroxyl groups, one of $R^{5'}$ or $R^{6'}$ is a single bond and the other is a hydrogen atom, and —O—R—O—, R', I, m and n are the same as defined above.

DETAILED DESCRIPTION OF THE INVENTION

The ganglioside of the present invention is characterized in that the fluorescent dye as a label is introduced in the ceramide moiety of the ganglioside.

The kind of fluorescent dye is not limited. Preferable examples of the fluorescent dye are fluorescein, 7-hydroxycoumarin, 7-aminocoumarin, 2,4-dinitrophenyl, pyrene, anthracene, acridine, cascade blue, rhodamine, 4-benzoylphenyl, Rosamine, 7-nitrobenz-2-oxa-1,3-diazole, 4,4-difluoro-4-bora-3a,4a-diaza-3-indacene, 5-azidonaphthalene, and the like. These fluorescent dyes may have substituents.

The fluorescent dye is amide bonded to the ceramide moiety through the ether, sulfide, amide, urethane, thiourea or amino group and also a methylene chain. The number of carbon atoms in the methylene chain interposed between the amide linkage and the labeling dye is between 2 and 20, preferably between 5 and 10.

Examples of the saccharide chain constituting the ganglioside according to the present invention, that is, —O—R—O— in the formulas (I) and (II) are β-D-O-galactopyranosyl-(1→4)-β-D-glucopyranosyl, O-(2-acetamide-2-deoxy-β-D-galactopyranosyl)-(1→4)-O-β-D-galactopyranosyl-(1→4)-β-D-glucopyranosyl, O-β-D-galactopyranosyl-(1→3)-O-(2-acetamide-2-deoxy-β-D-galactopyranosyl-(1→4)-O-β-D-galactopyranosyl-(1→4)-β-D-glucopyranosyl, O-β-D-galactopyranosyl-(1→3)-O-(2-acetamide-2-deoxy-β-D-glucopyranosyl-(1→3)-O-β-D-galactopyranosyl-(1→4)-β-D-glucopyranosyl, O-β-D-galactopyranosyl-(1→4)-O-(2-acetamide-2-deoxy-β-D-glucopyranosyl-(1→3)-O-β-D-galactopyranosyl-(1→4)-β-D-glucopyranosyl, O-(2-acetamide-2-deoxy-β-D-galactopyranosyl)-(1→4)-O-α-D-galactopyranosyl-(1→4)-O-β-D-galactopyranosyl-(1→4)-β-D-glucopyranosyl, O-(2-acetamide-2-deoxy-β-D-galactopyranosyl)-(1→4)-O-α-D-galactopyranosyl-(1→3)-O-β-D-galactopyranosyl-(1→4)-β-D-glucopyranosyl, O-β-D-galactopyranosyl-(1→4)-O-(O-α-L-fucosyl-(1-3))-(2-acetamide-2-deoxy-β-D-glucopyranosyl)-(1→3)-O-β-D-galactopyranosyl-(1→4)-O-β-D-glucopyranosyl, or O-β-D-galactopyranosyl-(1→3)-O-(O-α-L-fucosyl-(1-4))-(2-acetamide-2-deoxy-β-D-glucopyranosyl)-(1→3)-O-β-D-galactopyranosyl-(1→4)-O-β-D-glucopyranosyl The compound of the formula (I) according to the present invention may be synthesized by the following reaction steps:

First, a compound of the formula (VII):

wherein —O—R—O— is a saccharide chain constituting the ganglioside, one of $R^{5'}$ or $R^{6'}$ is a single bond and the other is a hydrogen atom, $R^{3'}$, $R^{7'}$, $R^{8'}$ and $R^{9'}$ are protecting groups for hydroxyl groups, $R^{2'}$ is a protecting group for a carboxylic acid, and n is an integer of 0 to 12 is condensed with a compound of the formula (VII):

HOOC—(CH$_2$)$_m$—R'  (VIII)

wherein m is an integer of at least 2, and R' is an ether, sulfide, amide, urethane, thiourea or amino group having a fluorescent dye to obtain a ganglioside of the formula (II):

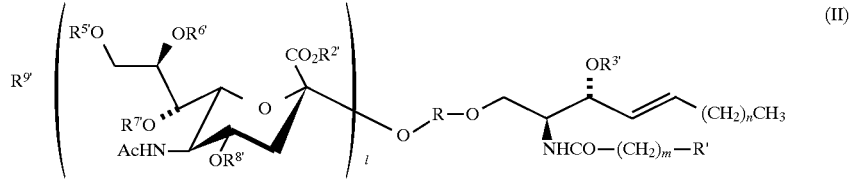

(II)

wherein —O—R—O—, R', $R^{2'}$, $R^{3'}$, $R^{5'}$, $R^{6'}$, $R^{7'}$, $R^{8'}$, $R^{9'}$, l, m and n are the same as defined above.

Examples of the protecting group for the hydroxyl group in the compound of the formula (VII) are ester groups such as an acetyl, benzoyl and pivaloyl groups, and examples of the protecting group for the carboxylic acid are lower alkyl groups such as a methyl, ethyl, propyl and butyl groups, and a benzyl group.

The compound of the formula (VII) may be prepared as follows:

The saccharide chain portion (—O—R—O—) is synthesized by protecting hydroxyl groups of at least one monosaccharide selected from the group consisting of D-glucose, D-galactose, N-acetyl-D-glucosamine, N-acetyl-D-galactosamine, L-fucose, lactose and N-acetyllactosamine, and condensing the protected monosaccharide by the glycosidation method (see, for example, the Journal of the Organic Synthesis Society (YUKI GOSEI KYOKAI-SHI), Vol. 60 (1992) 378–400).

The obtained saccharide chain is condensed with methyl (methyl-5-acetamide-4,7,8,9-tetra-O-acetyl-3,5-dideoxy-2-thio-D-glycero-α-D-galacto-2-nonulopiranosid)onate in the presence of an activating agent such as N-iodo-succinimide/trifluoromethane-sulfonic acid or dimethyl methylthiosulfonium triflate. When I is 2 or larger, the obtained sialic acid to which the saccharide chain has been bonded is condensed with the above compound in the same manner as above to add the sialic acid successively. Then, the sialylated saccharide chain is deprotected at the reducing terminal, and a sialylated saccharide chain of the formula:

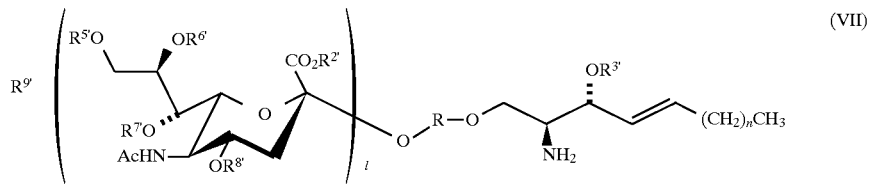

(VII)

$$\left( R^{9'} \underset{AcHN}{\overset{OR^{5'}}{\underset{R^{7}O^{\text{w}}}{\bigvee}}} \underset{OR^{8'}}{\overset{OR^{6'}}{\bigvee}} \underset{O}{\overset{CO_2R^{2'}}{\bigvee}} O \right)_l R-OH$$

wherein —O—R—O—, $R^{2'}$, $R^{5'}$, $R^{6'}$, $R^{7'}$, $R^{8'}$, $R^{9'}$ and $l$ are the same as defined above, is obtained.

The hydroxyl group at the saccharide chain end of this compound is activated with an activatable substituent, for example, by trichloroacetimidation, and then condensed with an azidosphingosine of the formula:

$$HO \underset{N_3}{\overset{OR^3}{\bigvee}} (CH_2)_m CH_3$$

wherein $R^3$ and m are the same as defined above, which has been synthesized by the method described by K. C. Nicolaus in Carbohydr. Res., Vol. 202 (1990) 177–191, and an azide compound of the formula (X):

$$\left[ R^{9'} \underset{AcHN}{\overset{R^{5'}O}{\underset{R^{7}O^{\text{w}}}{\bigvee}}} \underset{OR^{8'}}{\overset{OR^{6'}}{\bigvee}} \underset{O}{\overset{CO_2R^{2'}}{\bigvee}} O-R-O \underset{N_3}{\overset{OR^{3'}}{\bigvee}} (CH_2)_n CH_3 \right]_l$$ (X)

wherein $R^{2'}$, $R^{3'}$, $R^{5'}$, $R^{6'}$, $R^{7'}$, $R^{8'}$, $R^{9'}$, $l$ and $n$ are the same as defined above, is obtained.

Then, the azido group of this compound is converted to an amino group with a triphenylphosphine/water system or a hydrogen sulfide/pyridine system, and the compound of the formula (VII) is obtained. The example of this synthesis is described in JP-A-3-101691, page 4, lower right column, line 7 to page 9, upper right column, line 3.

The compound of the formula (VIII) may be prepared as follows:

First, an iodomethyl (—CH$_2$I), isocyanate (—NCO), thioisocyanate (—NCS), amino (—NH$_2$) or carboxyl (—COOH) group is introduced into the fluorescent dye such as fluorescein, 7-hydroxycoumarin, 7-aminocoumarin, 2,4-dinitrophenyl, pyrene, anthracene, acridine, cascade blue, rhodamine, 4-benzoylphenyl, Rosamine, 7-nitrobenz-2-oxa-1,3-diazole, 4,4-difluoro-4-bora-3a,4a-diaza-3-indacene, 5-azidonaphthalene, and the like. The methods for introducing such groups are known, and compounds into having such groups are commercially sold and easily obtained.

Then, the above obtained compound is bonded to a dicarboxylic acid (a), ω-amino acid (b), ω-hydroxycarboxylic acid (c) or ω-thiolcarboxylic acid (d) of the formula:

HOOC(CH$_2$)$_m$COOH        (a)

HOOC(CH$_2$)$_m$NH$_2$        (b)

HOOC(CH$_2$)$_m$OH        (c)

or HOOC(CH$_2$)$_m$SH        (d)

wherein m is an integer of at least 2.

The fluorescent dye having the iodomethyl group reacts with the amino group of the amino acid (b), the OH group of the hydroxycarboxylic acid (c) or the thiol group of the thiolcarboxylic acid (d) to form the amino bond, ether bond or sulfide bond, respectively. The fluorescent dye having the thioisocyanate group reacts with the amino group of the amino acid (b) to form the thiourea bond. The fluorescent dye having the amino group is condensed with the carboxyl group of the dicarboxylic acid (a) in the presence of a dehydrating agent such as dicyclohexylcarbodiimide to form the amide group. The fluorescent dye having the carboxyl group is condensed with the amino acid (b) to form the amide bond.

Accordingly, a compound of the formula (VIII):

HOOC—(CH$_2$)$_m$—R'        (VIII)

wherein m is an integer of at least 2, and R' is an ether, sulfide, amide, urethane, thiourea or amino group having a fluorescent dye is obtained.

The above reactions can be performed according to the conventional methods in the organic syntheses.

Next, the amino group of the compound of the formula (VII) is condensed with the carboxyl group of the compound of the formula (VIII) in the presence of a dehydrating agent such as dicyclohexylcarbodiimide (DCC), diisopropylcarbodiimide (DIPC), N-ethyl-N'-3-dimethylaminopropylcarbodiimide (WSCI), and the like, and the compound of the formula (II) is obtained.

The molar ratio of the compound of the formula (VII) to the compound of the formula (VIII) in the above reaction is between 1:0.5 and 1:2.0, preferably between 1:1 and 1:1.1.

The dehydrating agent is used in an amount of between 1 and 2 moles, preferably between 1 and 1.1 moles per one mole of the compound of the formula (VII).

Examples of preferably used solvents are dichloromethane, chloroform, dichloroethane, dimethylformamide, and the like.

The reaction temperature is usually between 15° and 25° C.

After the completion of the reaction, the reaction mixture is post-treated by, for example, extraction or evaporation of the solvent. The product may be purified by column chromatography, if necessary.

Alternatively, the compound of the formula (II) may be prepared by activating the carboxyl group of the compound of the formula (VIII) and then reacting the activated carboxyl group with the amino group of the compound of the formula (VII) according to the conventional method for the peptide synthesis, instead of the direct condensation between the compound of the formula (VII) and the compound of the formula (VIII) in the presence of the dehydrating agent such as DCC. The carboxyl group can be activated by the conventional methods such as the formation of an active ester with N-hydroxysuccinimide or p-nitrophenol, the mixed acid anhydride method, and the like.

The method using N-hydroxysuccinimide will be explained by way of example.

The compound of the formula (VII) is reacted with N-hydroxysuccinimide in the presence of a dehydrating agent such as DCC to obtain a N-hydroxysuccinimide ester of the formula (IX):

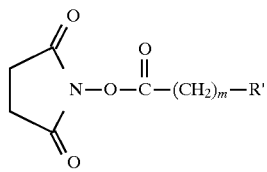

wherein m is the same as defined above.

This compound of the formula (IX) and the compound of the formula (VII) are condensed to obtain the compound of the formula (II). The compound of the formula (IX) is used in an amount of between 1 to 10 moles per one mole of the compound of the formula (VII). No catalyst may be necessary in general, although organic bases such as pyridine, triethylamine, etc. or inorganic bases such as sodium carbonate, potassium carbonate, etc. may be used as catalysts.

Aprotic solvents such as dichloromethane, dichloroethane, chloroform, ethyl acetate, dimethylformamide, and the like can be used as reaction media. The reaction temperature is between 0° and 40° C.

Then, the protecting groups for the hydroxyl and carboxyl groups of the compound of the formula (II) are removed, and the ganglioside (I) labeled with the fluorescence according to the present invention is obtained.

The above deprotection reaction can be performed as follows:

The compound of the formula (II) is dissolved in anhydrous methanol, and the two to four times molar equivalents of sodium methoxide is added to the solution. Then, the mixture is reacted at 50° C. for 30 minutes to 10 hours to remove the protecting groups for the hydroxyl and carboxyl groups. The reaction mixture is cooled to 0° C., and water is added to the mixture and stirred for 1 to 6 hours at the same temperature. The mixture is desalted with a H type cation exchange resin and then purified with a column containing SEPHADEX LH-20 to obtain the ganglioside (I) labeled with the fluorescent dye.

The preparation of fluorescein ganglioside GM3 as one of the ganglioside labeled with the fluorescent dye according to the present invention will be explained.

First, a compound of the formula (III):

wherein n is an integer of 0 to 12, $R^1$, $R^{11}$, $R^{12}$, $R^{13}$, $R^{14}$, $R^{15}$, $R^{16}$ and $R^3$ are protecting groups for the hydroxyl groups, and $R^2$ is a protecting group for the carboxyl group, is reacted with a compound of the formula (IV):

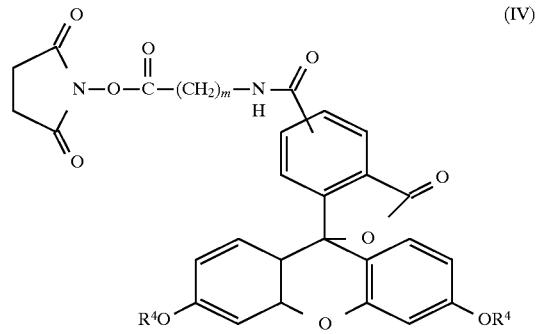

wherein m is an integer of at least 2, and $R^4$ is a protecting group for the hydroxyl group, and the compound of the formula (V):

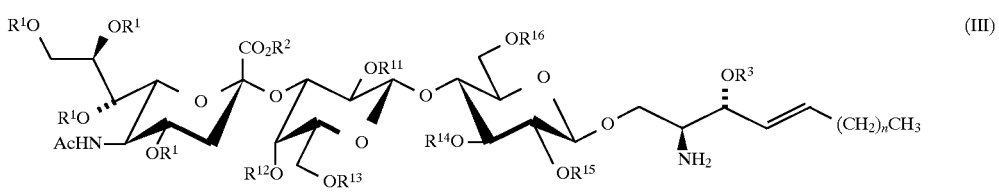

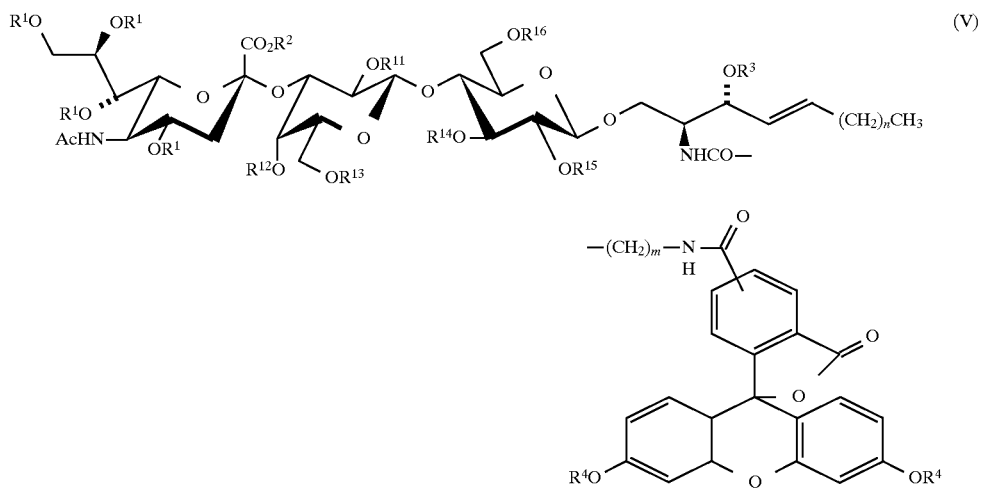

(V)

wherein $R^1$, $R^{11}$, $R^{12}$, $R^{13}$, $R^{14}$, $R^{15}$, $R^{16}$, $R^3$, $R^4$, m and n are the same as defined above.

The compound of the formula (IV) can be prepared as follows:

5-(or -6-)carboxyfluorescein and methyl ω-aminohexanoate hydrochloride are reacted in dimethylformamide in the presence of WSCI and pyridine, and 6-(fluorescein)-5 (or -6-)carboxamidehexanoic acid is obtained. This methyl ester is hydrolyzed with an alkali and then condensed with N-hydroxysuccinimide in the presence of WSCI as the carboxyl group source, and the compound of the formula (IV) is obtained.

Then, the protecting groups for the hydroxyl and carboxyl groups of the compound (V) are removed, and the fluorescein ganglioside GM3 of the following formula (VI) is obtained:

wherein m and n are the same as defined above.

EXAMPLES

The present invention will be illustrated by the following examples, which do not limit the scope of the present invention.

The abbreviations used in the results of NMR are as follows:

Me: Methyl group

Ac: Acetyl group

Ph: Phenyl group.

A ganglioside labeled with a fluorescent dye and an intermediate for the same of the present invention were prepared according to the following reaction scheme:

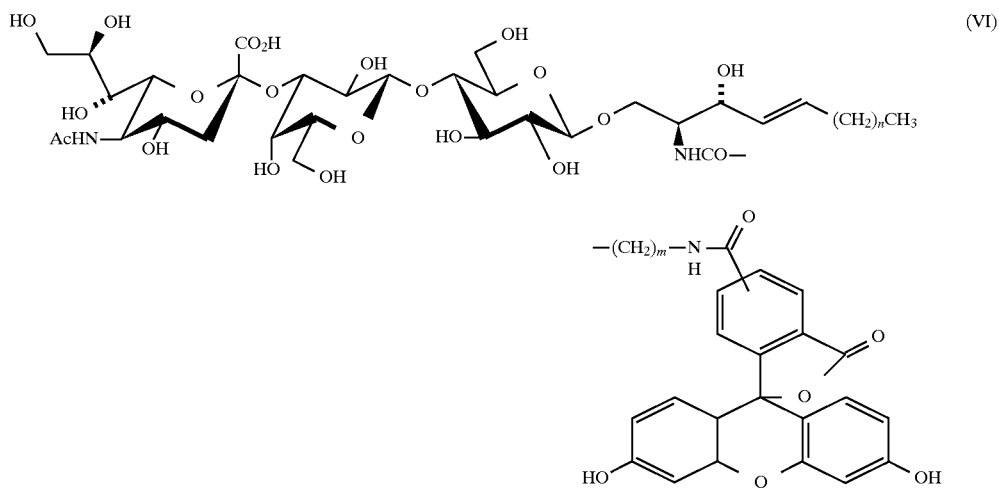

(VI)

Synthesis 1 of fluorescein ganglioside GM3
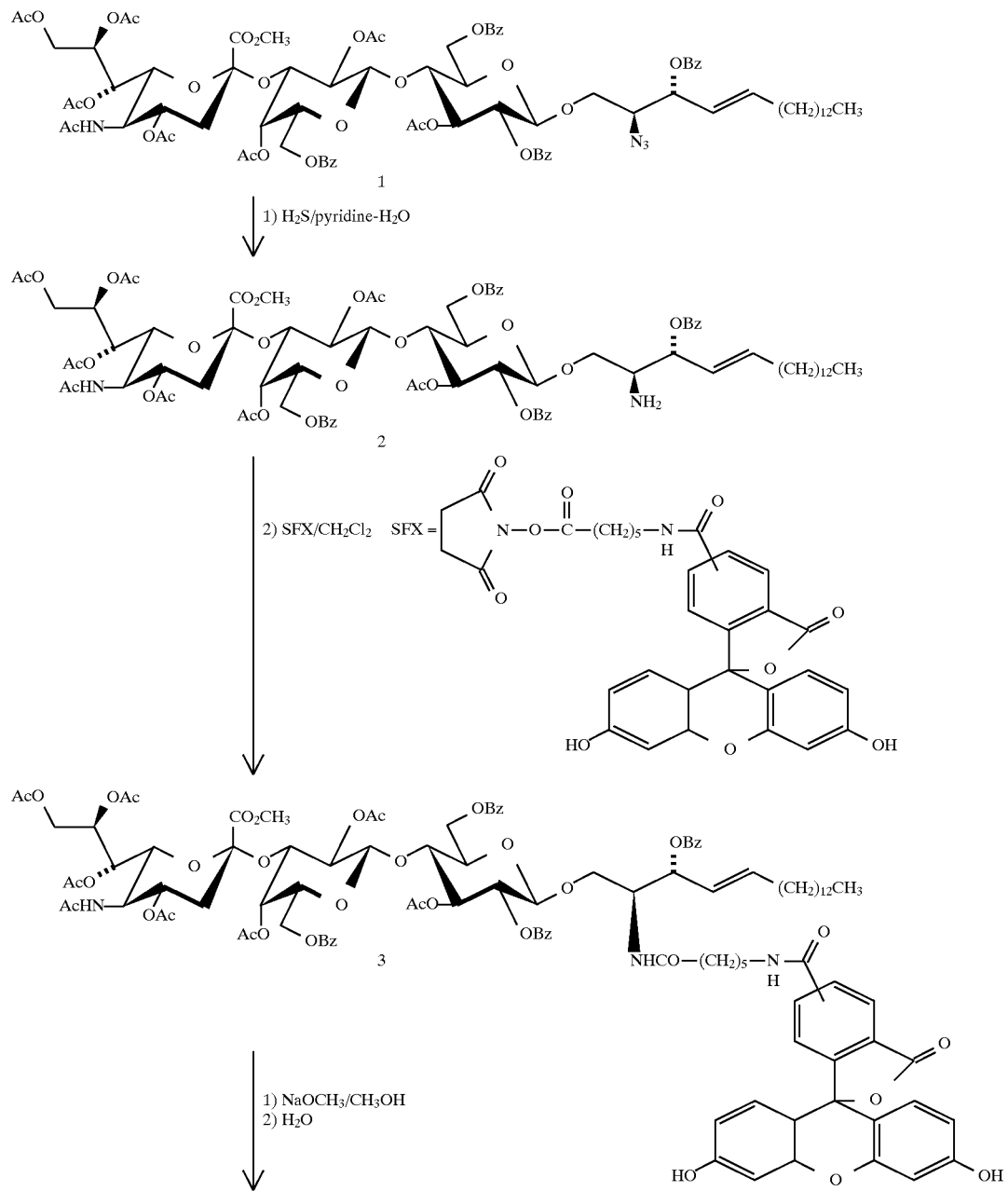

-continued
Synthesis 1 of fluorescein ganglioside GM3

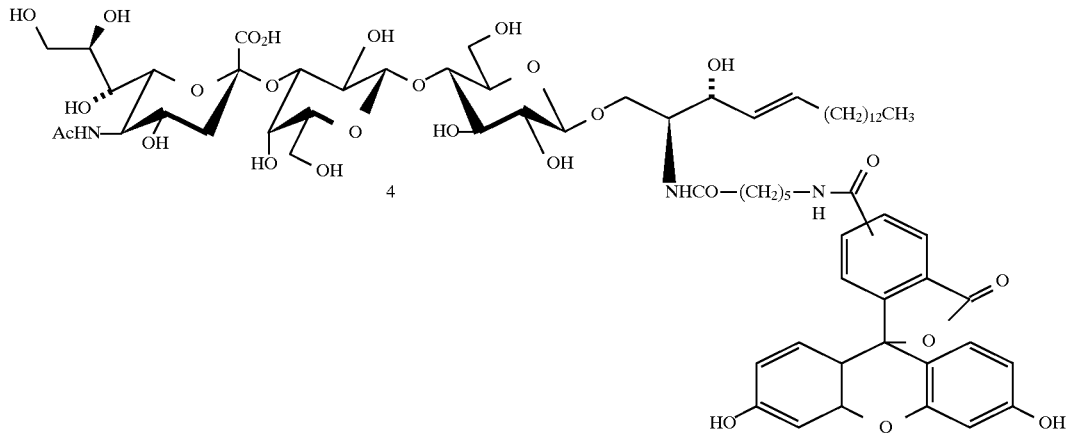

Example 1

Synthesis of O-(methyl 5-acetamide-4,7,8,9-tetra-O-acetyl-3,5-dideoxy-D-glycero-α-D-galacto-2-nonulopyranosylonate)-(2→3)-O-(2,4-di-O-acetyl-6-O-benzoyl-β-D-galactopyranosyl)-(1→4)-O-(3-O-acetyl-2,6-di-O-benzoyl-β-D-glucopyroanosyl) (1→1)-(2S,3R,4E)-3-O-benzoyl-2-[6-{fluorescein-5- (and -6-)-carboxamide}hexanamide]-4-octadecen-1,3-diol (the compound 3 in the above reaction scheme, hereinafter, referred to as the compound (3))

O-(Methyl 5-acetamide-4,7,8,9-tetra-O-acetyl-3,5-dideoxy-D-glycero-α-D-galacto-2-nonulopyranosylonic)-(2→3)-O-(2,4-di-O-acetyl-6-O-benzoyl-β-D-galactopyranosyl)-(1→4)-O-(3-O-acetyl-2,6-di-O-benzoyl-β-D-glucopyranosyl)(1→1)-(2S,3R,4E)-2-azido-3-O-benzoyl-4-octadecene-1,3-diol (the compound 1 in the above reaction scheme) (60 mg, 0.036 mmol) was dissolved in a mixed solvent of pyridine (5 ml) and water (1 ml). Hydrogen sulfide gas was bubbled through the solution at room temperature for 55 hours to reduce the azide group of the compound (1) to an amino group. After confirming the consumption of the raw material, hydrogen sulfide was removed from the reaction mixture, and then pyridine and water were evaporated off in vacuo.

The residue was dissolved in a mixed solvent of anhydrous dichloromethane (2 ml) and anhydrous N,N-dimethylformamide (1 ml), and succinimidyl 6-(fluorescein-5- (and -6-)-carboxamide)hexanoate (hereinafter referred to as SFX) (30 mg, 0.051 mmol) was added to the solution in an argon atmosphere, followed by stirring at room temperature for 18 hours. Further, SFX (47 ml, 0.080 mmol) was added, and the mixture was stirred at room temperature for 18 hours.

The reaction mixture was diluted with ethyl acetate, washed with water, dried over anhydrous sodium sulfate, and concentrated under reduced pressure. The residue was subjected to silica gel column chromatography (packing: silica gel 60 (7734), eluent: methanol/chloroform=1/15→1/10), and the compound (3) (35 mg) was obtained. Yield: 46%.

$IR_{max}^{KBr}(cm^{-1})$: 3430 (NH, OH), 2930, 2860 (Me, methylene) 1745, 1230 (ester), 1650, 1370 (amide), 710 (phenyl). NMR (CDCl$_3$; TMS):

Lactose unit: δ 4.59 (dd, J=10 Hz, H-3'), 4.67 (d, J=7.5 Hz, 1H, H-1), 4.83 (d, J=8 Hz, 1H, H-1'), 5.00 (d, 1H, J=4 Hz, H-4'), 5.01 (dd, J=10 Hz, 8 Hz, 1H, H-2'), 7.3–8.1 (m, 20H, 4×Ph).

Sialic acid unit: δ 1.66 (dd, J=13 Hz, 13 Hz, 1H, H-3α), 1.84 (s, 3H, N—COCH$_3$), 2.58 (dd, J=13 Hz, 5 Hz, 1H, H-3e), 3.70 (s, 3H, OCH$_3$), 4.86 (m, 1H, H-4).

Ceramide unit: δ 0.86 (t, J=7 Hz, 3H, CH$_3$), 1.3-1.1 (m, 26H, 13×CH$_2$), 5.50 (dd, J=15 Hz, 7 Hz, 1H, H-4), 5.67 (dt, J=15 Hz, 7 Hz, 1 H, H-5).

O-Acetyl group: δ 1.965, 1.975, 1.99(2), 2.01, 2.10, 2.18 (7s, 21H, 7×Ac).

Example 2

Synthesis of O-(5-acetamide-3,5-dideoxy-D-glycero-α-D-galacto-2-nonulopyranosilonic acid)-(2→3)-O-(β-D-galactopyranosyl)-(1→4)-O-β-D-glucopyranosyl)(1→1)-(2S,3R,4E)-2-[6-{fluorescein-5-(and -6-)-carboxamide}hexanamide]-4-octadecen-1,3-diol (the compound 4 in the above reaction scheme, hereinafter referred to as the compound (4)).

Sodium methoxide (10 mg, 0.185 mmol) was added to a solution of the compound (3) (34 mg, 0.016 mmol) in anhydrous methanol (2 ml) in an argon atmosphere and stirred at room temperature for 8 hours. After cooling to 0° C., water (0.2 ml) was added to the reaction mixture and stirred at 0° C. for 5.5 hours. The reaction mixture was subjected to the AMBERLITE IR 120 (H$^+$) column chromatography (eluent: methanol/water=9/1), and the eluted portion was evaporated under reduced pressure. The residue was subjected to column chromatography (packing: SEPHADEX LH-20, eluent: methanol), and the compound (4) (19 mg) was obtained.

Yield: 85%.

$[\alpha]_D^{25}=0.49°$ (c=0.21, 1:2 CHCl$_3$/CH$_3$OH). $IR_{max}^{KBr}$ (cm$^{-1}$): 3380 (OH, NH), 2930, 2855 (Me, methylene), 1745 (carbonyl) 1635, 1550 (amide). NMR (3:1 CD$_3$OD/CDCl$_3$, TMS):

Lactose unit: δ 4.30 (d, J=8 Hz, 1H, H-1), 4.42 (d, J=8 Hz, 1H, H-1').

Sialic acid unit: δ 2.02 (s, 3H, N-COCH$_3$), 2.76 (dd, J=13 Hz, 5 Hz, 1 H, H-3e).

Ceramide unit: δ 0.88 (t, J=7 Hz, 3H, CH$_2$CH$_3$), 1.3-1.1 (m, 26H, 13×CH$_2$), 2.24 (t, J=7 Hz, 2H, CH$_2$CO), 4.17 (dd, J=10 Hz, 5 Hz, 1H, H-1), 5.46 (dd, J=15 Hz, 7 Hz, 1H, H-4), 5.71 (dt, J=15 Hz, 1H, H-5).

Synthesis 2 of fluorescein ganglioside GM3

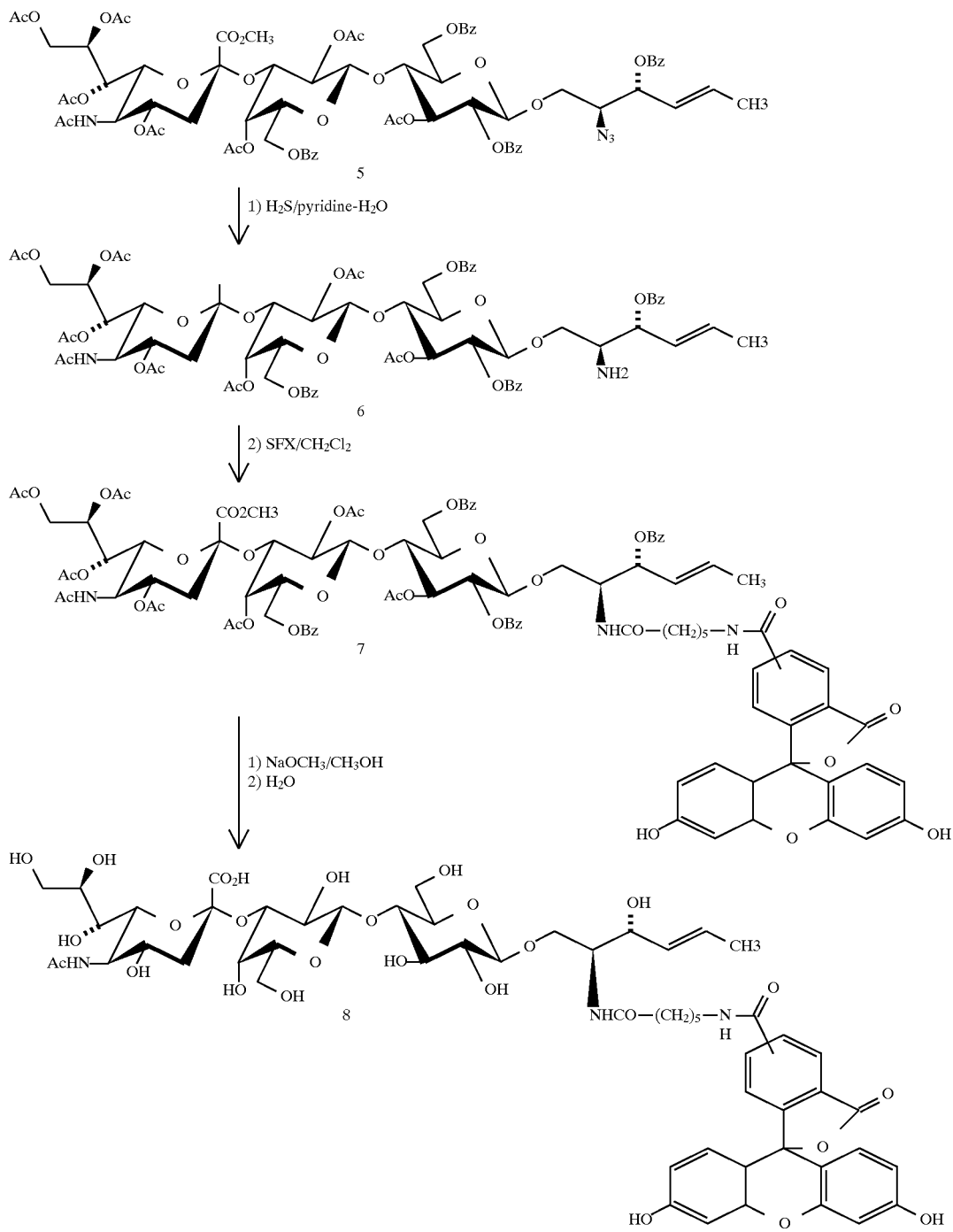

Example 3
Synthesis of O-(methyl 5-acetamide-4,7,8,9-tetra-O-acetyl-3,5-dideoxy-D-glycero-α-D-galacto-2-nonulopyrasylonate)-(2→3)-O-(2,4-di-O-acetyl-6-O-benzoyl-β-D-galactopyranosyl)-(1→4)-O-(3-O-acetyl-2,6-di-O-benzoyl-β-D-glucopyranosyl)(1→1)-(2S,3R,4E)-3-O-benzoyl-2-[6-{fluorescein-5- (and -6-)-carboxamide}hexanamide-4-hexen-1,3-diol (the compound 7 in the above reaction scheme, hereinafter referred to as the compound (7))

O-(methyl 5-acetamide-4,7,8,9-tetra-O-acetyl-3,5-dideoxy-D-glycero-α-D-galacto-2-nonulopyrasilonate)-(2→3)-O-(2,4-di-O-acetyl-6-O-benzoyl-β-D-galactopyranosyl)-(1→4)-O-(3-O-acetyl-2,6-di-O-benzoyl-β-D-glucopyranosyl)(1→1)-(2S,3R,4E)-2-azido-3-O-benzoyl-4-hexen-1,3-diol (the compound 5 in the above reaction scheme) (80 mg, 0.053 mmol) was dissolved in a mixed solvent of pyridine (8.9 ml) and water (1.8 ml). Hydrogen sulfide gas was bubbled through the solution at room temperature for 51 hours to reduce the azide group of the compound 5 to an amino group. After confirming the consumption of the raw material, hydrogen sulfide was removed from the reaction mixture, and then pyridine and water were evaporated off in vacuo.

The residue was dissolved in anhydrous N,N-dimethylformamide (4.5 ml), and SFX (37 mg, 0.064 mmol) was added to the solution in an argon atmosphere, followed by stirring at room temperature for 101 hours. The reaction mixture was diluted with ethyl acetate, washed with water, dried over anhydrous sodium sulfate, and concentrated under reduced pressure. The residue was subjected to the silica gel column chromatography (packing: silica gel 60 (7734), eluent: methanol/chloroform=1/30→1/20→1/10→1/5), and the compound (7) (42 mg) was obtained. Yield: 41%.

$IR_{max}^{KBr}(cm^{-1})$: 3390 (NH, OH), 2955 (methylene), 1745, 1230 (ester), 1645, 1370 (amide), 710 (phenyl). NMR ($CDCl_3$; TMS):

Lactose unit: δ 4.59 (dd, J=10 Hz, 3 Hz, 1H, H-3'), 4.67 (d, J=8 Hz, 1H, H-1), 4.85 (d, J=8 Hz, 1H, H-1'), 5.00 (d, 1H, J=3 Hz, H-4'), 5.01 (dd, J=10 Hz, 8 Hz, 1H, H-2'), 7.3–8.1 (m, 20H, 4×Ph).

Sialic acid unit: δ 1.68 (dd, J=12 Hz, 12 Hz, 1H, H-3a) 1.84 (s. 3H, N-$COCH_3$), 2.58 (dd, J=13 Hz, 5 Hz, 1 H, H-3e), 3.70 (s, 3H, $OCH_3$), 4.88 (m, 1H, H-4).

Ceramide unit: δ 1.3-1.1 (m, 4H, 2×$CH_2$), 1.52 (d, J=6 Hz, 3H, $CH_3$), 5.49 (dd, J=15 Hz, 9 Hz, 1H, H-4), 5.70 (dq, J=15 Hz, 7 Hz, 1 H, H-5).

O-Acetyl group: δ 1.97, 1.98, 1.985, 1.99, 2.00, 2.09, 2.16 (7s, 21H, 7×Ac).

Example 4

Synthesis of O-(5-acetamide-3,5-dideoxy-D-glycero-α-D-galacto-2-nonulopyranosylonic acid)-(2→3)-O-(β-D-galactopyranosyl)-(1→4)-O-(β-D-glucopyranosyl)(1→1)-(2S,3R,4E)-2-[6-{fluorescein-5- (and -6-)-carboxamide}hexanamide]-4-hexen-1,3-diol (the compound 8 in the above reaction scheme, hereinafter referred to as the compound (8))

Sodium methoxide (8 mg, 0.15 mmol) was added to the solution of the compound (7) (41 mg, 0.021 mmol) in anhydrous methanol (2 ml) and stirred at room temperature for 5.5 hours. After cooling to 0° C., water (0.2 ml) was added to the reaction mixture and stirred at 0° C. for 3 hours.

The reaction mixture was subjected to the AMBERLITE IR 120 ($H^+$) column chromatography (eluent: methanol/water=1/1), and the eluted portion was evaporated under reduced pressure. The residue was subjected to column chromatography (packing: SEPHADEX LH-20, eluent: methanol), and the compound (8) (23 mg) was obtained. Yield: 89%.

$[\alpha]_D^{25}$=−0.48° (c=0.21, 1:2 $CHCl_3/CH_3OH$). $IR_{max}^{KBr}$ ($cm^{-1}$): 3385 (OH, NH), 2935 (methylene), 1745 (carbonyl) 1640, 1560 (amide). NMR (3:1 $CD_3OD/CDCl_3$, TMS):

Lactose unit: δ 4.31 (d, J=8 Hz, 1H, H-1), 4.42 (d, J=8 Hz, 1H, H-1').

Sialic acid unit: δ 2.01 (s, 3H, N-$COCH_3$), 2.76 (dd, J=13 Hz, 4.5 Hz, 1H, H-3e).

Ceramide unit: δ 1.3-1.1 (m, 4H, 2×$CH_2$), 1.69 (d, J=7 Hz, 3H, $CH_3$), 2.24 (t, J=7 Hz, 2H, $CH_2CO$), 4.16 (dd, J=10 Hz, 5 Hz, 1H, H-1), 5.49 (d, J=15.5 Hz, 7 Hz, 1H, H-4), 5.71 (dq, J=15.5 Hz, 1H, H-5).

Effects of the Invention

The ganglioside labeled with the fluorescent dye according to the present invention has the synergistic effects achieved by the recognition characteristics of the saccharide chain portion and the labeling property of the fluorescent dye introduced in the ceramide moiety, and is useful as an agent for monitoring the dynamic behavior of the receptor for glycolipids, a diagnostic agent for bacteria or viruses, and the like.

We claim:

1. A process for preparing a fluorescein ganglioside GM3 of the formula (VI):

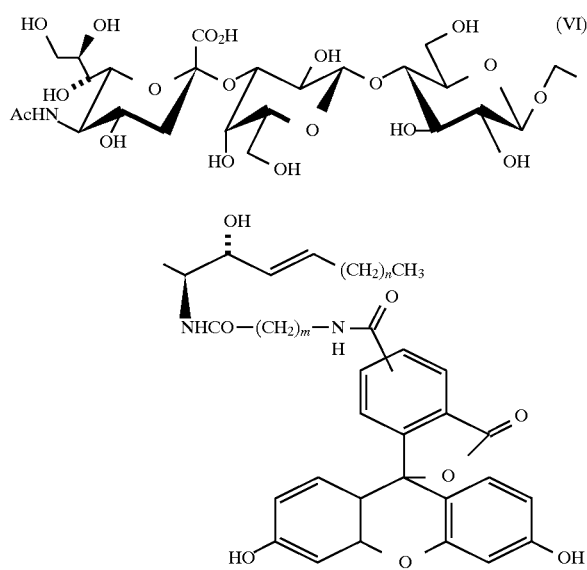

wherein m is an integer of at least two and n is an integer of 0 to 12, comprising the steps of reacting a compound of the formula (III):

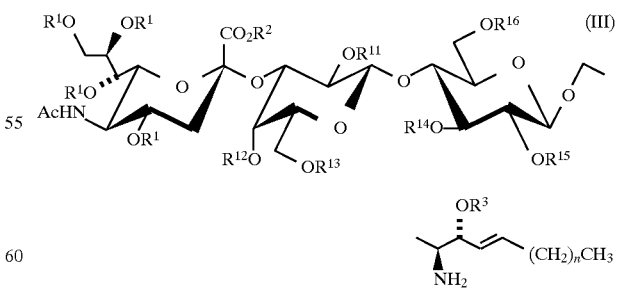

wherein n is an integer of 0 to 12, $R^1$, $R^{11}$, $R^{12}$, $R^{13}$, $R^{14}$, $R^{15}$, $R^{16}$ and $R^3$ are protecting groups for the hydroxyl groups, and $R^2$ is a protecting group for the carboxyl group with a compound of the formula (IV):

(IV)

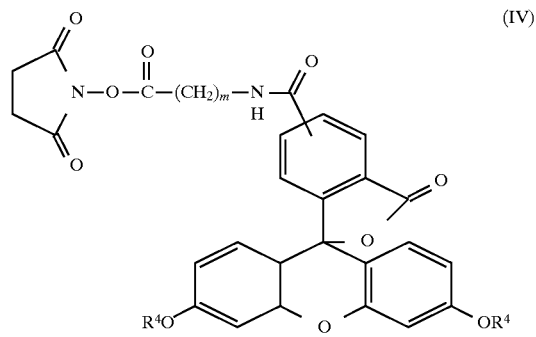

wherein m is an integer of at least two, and $R^4$ is a protecting group for the hydroxyl group to obtain a compound of the formula (V):

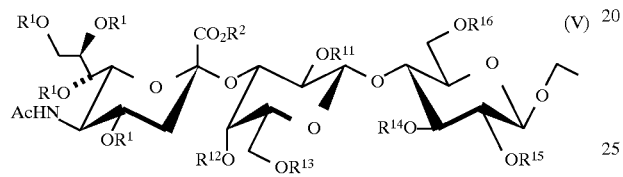

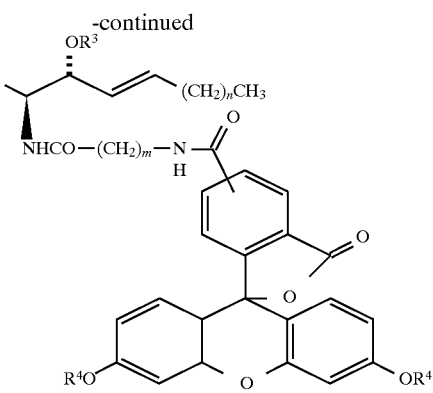

wherein $R^1$, $R^{11}$, $R^{12}$, $R^{13}$, $R^{14}$, $R^{15}$, $R^{16}$, $R^3$, $R^4$, m and n are the same as defined above, and removing the protecting groups for the hydroxyl and carboxyl groups in the compound of the formula (V) to obtain the fluorescein ganglioside GM3.

2. The method according to claim 1, wherein m is 1 and n is 0.

3. The method according to claim 1, wherein m is 5 and n is 12.

* * * * *